(12) United States Patent
Chu et al.

(10) Patent No.: US 11,141,542 B2
(45) Date of Patent: Oct. 12, 2021

(54) SUB-ASSEMBLY, A MEDICAMENT DELIVERY DEVICE AND A METHOD OF ASSEMBLING A SUB-ASSEMBLY

(71) Applicant: Carebay Europe Ltd., Sliema (MT)

(72) Inventors: Chun Chu, Taipei (TW); Wen-Yen Lee, Taoyuan (TW); Hsuan Wang, Taoyuan (TW)

(73) Assignee: SHL MEDICAL AG, Zug (CH)

( * ) Notice: Subject to any disclaimer, the term of this patent is extended or adjusted under 35 U.S.C. 154(b) by 324 days.

(21) Appl. No.: 16/341,424

(22) PCT Filed: Sep. 25, 2017

(86) PCT No.: PCT/EP2017/074257
§ 371 (c)(1),
(2) Date: Apr. 11, 2019

(87) PCT Pub. No.: WO2018/069031
PCT Pub. Date: Apr. 19, 2018

(65) Prior Publication Data
US 2020/0038598 A1    Feb. 6, 2020

(30) Foreign Application Priority Data
Oct. 13, 2016 (EP) .................................... 16193816

(51) Int. Cl.
*A61M 5/32* (2006.01)
*A61M 15/00* (2006.01)

(52) U.S. Cl.
CPC ...... *A61M 5/3204* (2013.01); *A61M 15/0025* (2014.02); *A61M 2207/00* (2013.01)

(58) Field of Classification Search
CPC .. A61M 5/3204; A61M 5/3202; A61M 5/321; A61M 5/3213; A61M 5/3205; A61M 15/0025; A61M 2005/3215
See application file for complete search history.

(56) References Cited

U.S. PATENT DOCUMENTS 8,992,477 B2    3/2015  Raday et al.
2010/0268169 A1*  10/2010  Llewellyn-Hyde ..................
                                                      A61M 5/5086
                                                           604/192
(Continued)

FOREIGN PATENT DOCUMENTS

CN          1973912 A    6/2007
CN        103491998 A    1/2014
(Continued)

OTHER PUBLICATIONS

"Definition of Receive", Merriam-Webster Online Dictionary, <https://www.merriam-webster.com/dictionary/receive>. (Year: 2021).*
(Continued)

*Primary Examiner* — Nathan R Price
*Assistant Examiner* — Tasnim Mehjabin Ahmed
(74) *Attorney, Agent, or Firm* — McDonnell Boehnen Hulbert & Berghoff LLP

(57) ABSTRACT

A sub-assembly for a medicament delivery device is presented having a cap provided with a distal opening and configured to be mounted to a proximal end of the medicament delivery device. A tubular remover is received in the distal opening of the cap, the remover having a proximal end portion fixedly attached to the cap, a housing with an internal structure and provided with a proximal inclined surface. The remover has a plurality of radially flexible legs extending longitudinally from a proximal end of the remover to a distal end thereof, each leg having a gripper that engages with a delivery member shield of the medicament delivery device and having a guide finger configured to extend distally beyond the grippers or cooperating with an internal structure of the medicament delivery device to guide radial expansion of the legs when the remover is mounted in the medicament delivery device.

19 Claims, 6 Drawing Sheets

(56) References Cited

U.S. PATENT DOCUMENTS

| | | | |
|---|---|---|---|
| 2012/0191047 A1* | 7/2012 | Raday | A61M 5/2033 604/198 |
| 2014/0343503 A1* | 11/2014 | Holmqvist | A61M 5/3202 604/192 |
| 2015/0051553 A1* | 2/2015 | Bjork | A61M 5/3287 604/198 |
| 2015/0272778 A1 | 10/2015 | Clarke et al. | |
| 2017/0014578 A1* | 1/2017 | Bunch | A61M 5/3257 |

FOREIGN PATENT DOCUMENTS

| | | |
|---|---|---|
| EP | 2774640 A1 | 9/2014 |
| EP | 2923716 A1 | 9/2015 |
| GB | 2465389 A | 5/2010 |
| WO | 2011012903 A1 | 2/2011 |
| WO | 2012103140 A1 | 8/2012 |
| WO | 2013135566 A2 | 9/2013 |
| WO | 2015144871 A1 | 10/2015 |
| WO | 2016/051168 A2 | 4/2016 |
| WO | 2016/135250 A1 | 9/2016 |
| WO | 2017029515 A1 | 2/2017 |

OTHER PUBLICATIONS

Chinese Office Action for CN Application No. 201780062588.5, dated Dec. 29, 2020.
Search Report issued in Chinese Patent Application No. 106133377 dated Nov. 27, 2018.

* cited by examiner

SUB-ASSEMBLY, A MEDICAMENT DELIVERY DEVICE AND A METHOD OF ASSEMBLING A SUB-ASSEMBLY

CROSS REFERENCE TO RELATED APPLICATIONS

The present application is a U.S. National Phase Application pursuant to 35 U.S.C. § 371 of International Application No. PCT/EP2017/074257 filed Sep. 25, 2017, which claims priority to European Patent Application No. 16193816.2 filed Oct. 13, 2016. The entire disclosure contents of these applications are hereby incorporated by reference into the present application.

TECHNICAL FIELD

The present disclosure generally relates to medical devices. In particular, it relates to a sub-assembly for a medicament delivery device, to a medicament delivery device comprising the sub-assembly, and to a method of assembling the sub-assembly.

BACKGROUND

Medicament delivery devices, such as injectors and inhalers, typically comprise a housing in which a medicament container containing a medicament is to be arranged. Upon activation of the medicament delivery device, the medicament is expelled through a medicament delivery member, for example a needle or a nozzle.

In order to protect and to keep the medicament delivery member sterile, the medicament delivery member may be provided with a delivery member shield, or sheath, such as a Flexible Needle Shield (FNS) or a Rigid Needle Shield (RNS). The delivery member shield may thus be attached to the medicament container to cover the delivery member.

Moreover, the medicament delivery device may comprise a removable cap which is mounted to the proximal end of the housing, i.e. that end which is placed towards the injection site during medicament delivery, of the medicament delivery device, or to the proximal end of the medicament container. The removable cap has the function of providing mechanical protection of the medicament delivery member while attached to the housing or medicament container, and to remove the delivery member shield when the cap is removed from the housing.

An example of a sheath removal mechanism for removing a protective needle sheath from a medicament container in a medicament delivery device is disclosed in WO2015/144871 A1. The sheath removal mechanism comprises a cap attachable to a proximal end of the medicament delivery device. The cap comprises at least one ledge adapted to engage the protective needle sheath, and has a proximal opening. An assembly tool can be provided into the proximal opening from the front side of the cap to splay sheath removal beams on the inner side of the cap apart such that the protective needle sheath may be received between the sheath removal beams. By removing the assembly tool, the beams will no longer be splayed, and the ledge will thereby engage the protective needle sheath.

SUMMARY

According to the mechanism disclosed in WO2015/144871 A1 the cap has to be manipulated by means of the assembly tool to splay the sheath removal beams apart when the medicament container is being inserted into the case. This requires certain timing because the beams must be fully splayed apart when the needle sheath is to be received by the cap, as otherwise the needle sheath will make contact with the beams during insertion. Such contact is undesirable because the forces thus exerted onto the needle sheath may cause movement of the needle sheath relative to the needle which it encloses, which could potentially cause coring, i.e. that the needle becomes filled with debris from the needle sheath, and/or that the needle is bent.

In view of the above, a general object of the present disclosure is to provide a cap assembly for a medicament delivery device which solves or at least mitigates the problems of the prior art.

There is hence according to a first aspect of the present disclosure provided a cap assembly for a medicament delivery device, comprising: a cap having a tubular body provided with a distal opening, the cap being configured to be mounted to a proximal end of a medicament delivery device, and a tubular remover configured to be received in the distal opening of the cap, the remover having a proximal end portion configured to be fixedly attached to the cap, wherein the remover has a plurality of radially flexible legs extending axially from a proximal end of the remover to a distal end thereof, each leg having a gripper configured to engage with a delivery member shield of a medicament delivery device, and each leg having a guide finger configured to extend distally beyond the grippers for cooperating with an internal structure of a medicament delivery device to guide radial expansion of the legs when the remover is mounted in a medicament delivery device.

The remover, or de-shielder, is configured to receive a delivery member shield. Hereto, when a medicament delivery device is fully assembled, including the cap assembly, the delivery member shield extends inside the tubular remover. The legs of the remover are expanded radially until the cap assembly is removed, i.e. pulled in the proximal direction, from the main body of the medicament delivery device. In particular, the guide fingers are configured to cooperate with an internal structure, a proximal inclined surface, located inside the medicament delivery device, which urges the legs apart when the remover is pushed in the distal direction into the housing of the medicament delivery device, to obtain a state in which the legs are fixed in the radially extended position until the cap assembly is pulled forward in the proximal direction for removal thereof. This allows for insertion of a medicament container assembly, comprising a delivery member shield, from the distal direction into the main body or housing of the medicament delivery device, without risking that the delivery member shield contacts the remover when received therein. Hence, no coring will be able to occur at this stage of the assembly procedure. When the cap assembly is removed from the main body of the medicament delivery device, radial contraction, or radial inwards movement of the legs causes the grippers to move radially inwards and engage with the delivery member shield. The delivery member shield will hence be removed concurrently with the cap assembly.

According to one embodiment each gripper extends radially inwards to allow engagement with a delivery member shield.

According to one embodiment each gripper has a hook-like structure.

According to one embodiment each guide finger extends radially outwards. In particular, according to one variation, the gripers are bent radially inwards to enable gripping of a delivery member shield received in the remover, and the guide fingers, which extend distally beyond the grippers, are bent radially outwards, to guide the degree of radial expansion of the remover when cooperating with a proximal radial surface, a sloping surface, arranged inside the medicament delivery device.

According to one embodiment each guide finger gradually increases the diameter of the remover in the distal direction. Hence, each guide finger is sloping or is inclined relative to the central axis of the remover.

According to one embodiment for each leg the angle between the gripper and the leg is a and the angle between the guide finger and the leg is essentially 180°-α. The grippers and the guide fingers hence essentially have the same inclinations, although the grippers extend radially inwards and the guide fingers extend radially outwards. Alternatively, the grippers and the guide fingers could have different inclinations.

According to one embodiment each leg of the plurality of legs is oppositely arranged to another leg of the plurality of legs.

According to one embodiment each guide finger is located adjacent to, in the circumferential direction, a gripper.

According to one embodiment each leg has a distal end portion, wherein each gripper is provided on the distal end portion of a respective leg, enabling engagement with a distal edge of a delivery member shield.

There is according to a second aspect of the present disclosure provided a sub-assembly for a medicament delivery device, which sub-assembly comprises: a housing, an internal structure arranged inside the housing and provided with a proximal inclined surface, and a cap assembly according to the first aspect.

According to one embodiment the guide fingers are configured to cooperate with the proximal inclined surface of the internal structure, to maintain a radial expansion of the legs of the remover.

According to one embodiment the proximal inclined surface has a first inclination relative to a central axis of the housing, and wherein the guide fingers have the same inclination as the proximal inclined surface has.

According to one embodiment the proximal inclined surface provides an increasing diameter of the internal structure in the distal direction.

There is according to a third aspect of the present disclosure provided a medicament delivery device comprising a sub-assembly according to the second aspect.

There is according to a fourth aspect of the present disclosure provided a method of assembling a sub-assembly of a medicament delivery device, comprising: a) providing a cap assembly comprising: a cap having a tubular body provided with a distal opening, the cap being configured to be mounted to a proximal end of a medicament delivery device, and a tubular remover received in the distal opening of the cap, the remover having a proximal end portion fixedly attached to the cap, wherein the remover has a plurality of radially flexible legs extending axially from a proximal end of the remover to a distal end thereof, each leg having a gripper configured to engage with a delivery member shield of a medicament delivery device, and each leg having a guide finger configured to extend distally beyond the grippers for cooperating with an internal structure of a medicament delivery device to guide radial expansion of the legs when the remover is mounted in a medicament delivery device, a housing, and an internal structure arranged inside the housing, and provided with a proximal inclined surface, b) assembling the cap with the housing by pushing the remover into the housing, c) expanding the remover radially by means of an assembly tool inserted into the housing from a distal end thereof, d) pushing the guide fingers against the proximal inclined surface of the internal structure whereby the legs of the remover maintain their expanded position, and e) removing the assembly tool from the housing.

Generally, all terms used in the claims are to be interpreted according to their ordinary meaning in the technical field, unless explicitly defined otherwise herein. All references to "a/an/the element, apparatus, component, means, etc. are to be interpreted openly as referring to at least one instance of the element, apparatus, component, means, etc., unless explicitly stated otherwise.

BRIEF DESCRIPTION OF THE DRAWINGS

The specific embodiments of the inventive concept will now be described, by way of example, with reference to the accompanying drawings, in which:

FIG. 7b shows a close-up view of a portion of the sub-assembly in FIG. 7a;

DETAILED DESCRIPTION

Figure 1:
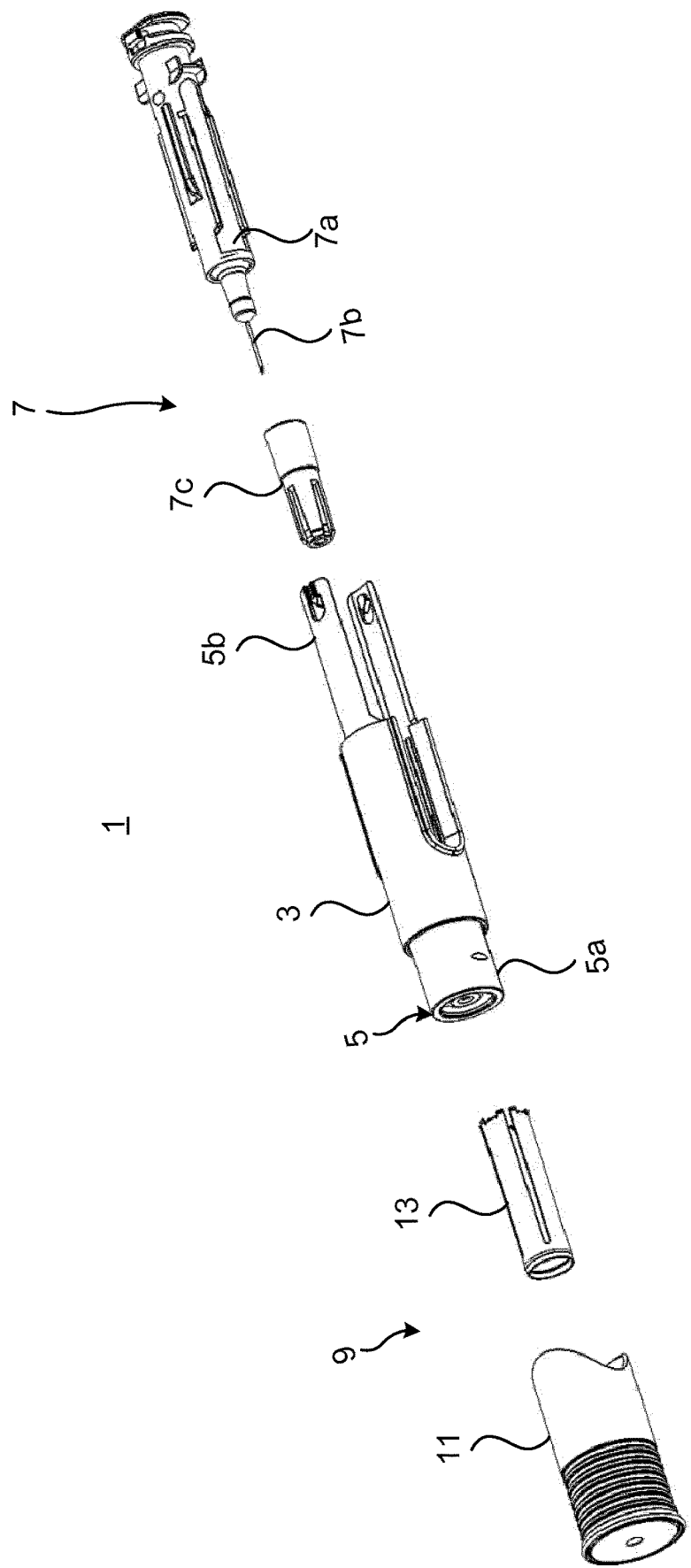
FIG. 1 is an exploded view of an example of a medicament delivery device, showing some parts thereof.

The inventive concept will now be described more fully hereinafter with reference to the accompanying drawings, in which exemplifying embodiments are shown. The inventive concept may, however, be embodied in many different forms and should not be construed as limited to the embodiments set forth herein; rather, these embodiments are provided by way of example so that this disclosure will be thorough and complete, and will fully convey the scope of the inventive concept to those skilled in the art. Like numbers refer to like elements throughout the description.

The term "proximal end" as used herein, when used in conjunction with a cap assembly, refers to that end of the cap assembly which is farthest from the proximal end of the medicament delivery device, when the cap assembly is properly mounted onto a medicament delivery device. The proximal end of a medicament delivery device is that end which is to be pointed towards the injection site during medicament injection. The same considerations also apply when referring to any component of the cap assembly. The "distal end" is the opposite end relative to the proximal end. With "proximal direction" and, equivalently, "proximally" is meant a direction from the distal end towards the proximal end, along the central axis of the safety mechanism. With "distal direction" or "distally" is meant the opposite direction to "proximal direction". The same definition also applies for the medicament container and any component thereof.

According to one aspect, the present disclosure relates to a cap assembly for a medicament delivery device, for example an auto-injector. The cap assembly comprises a cap and a tubular remover. The cap has a tubular body provided with a distal opening, and the remover is configured to be received in the distal opening. Hereto, the remover and the cap have a coaxial extension when the remover is mounted in the cap. The remover is configured to receive a delivery member shield.

The remover has a plurality of axially extending radially flexible legs. Each leg extends from a proximal end to a distal end of the remover. By means of this design, the remover is able to expand radially when the legs are subjected to radially outwardly directed forces.

Furthermore, each leg is provided with a gripper. Each gripper is configured to engage with a delivery member shield of a medicament delivery device. Thereby, the delivery member shield can be removed from a medicament container concurrently with the removal of the cap, and the remover provided therein, from a medicament delivery device.

Each leg is provided with a guide finger. Each guide finger is configured to extend axially beyond the grippers. The guide fingers are intended to cooperate with an internal structure of a medicament delivery device, to thereby guide the amount of radial expansion of the legs. By radial expansion of the legs, and thus radial displacement of the grippers and guide fingers, a portion of the medicament container assembly, including the delivery member shield, is able to slide past the grippers and guide fingers during assembly without physical contact. Subsequently, when the cap assembly is to be removed from the main body of the medicament delivery device, upon proximal movement of the cap assembly relative to the main body, the guide fingers are released from contact with the internal structure of the medicament delivery device. The legs will thus contract radially, and the grippers will engage with the delivery member shield, thus removing the delivery member shield together with the cap assembly.

FIG. 1 shows an example of a medicament delivery device 1. It is to be noted that some parts of the medicament delivery device 1 depicted in FIG. 1 are not shown, most notably the "power pack", which is an assembly that is to be installed at a distal end of the medicament delivery device, and which contains the drive mechanism for medicament expulsion from a medicament container of the medicament delivery device 1.

Medicament delivery device 1 comprises a housing or main body 3, of which for illustrative purposes only a proximal portion is shown, and a proximally biased delivery member cover 5 which has a tubular proximal portion 5a. The delivery member cover 5 is configured to be displaced relative to the housing 3, from an extended position relative to the housing 3, in which the delivery member cover 5 extends proximally from the housing 3, to a retracted position, in which the delivery member cover 5 has been displaced in the distal direction and further received by the housing 3.

The previously mentioned "power pack" may for example include a plunger rod, and a moveable sleeve which is configured to engage with and cooperate with a distal end 5b of the delivery member cover 5, such that linear displacement of the delivery member cover 5 in the distal direction, i.e. from the extended position to the retracted position, is translated to rotational motion of the movable sleeve, thereby releasing the plunger rod, enabling it to move in the proximal direction. Medicament expulsion may thus be initiated. The "power pack" will not be described in any further detail herein.

The exemplified medicament delivery device 1 also includes a medicament container assembly 7, which includes a medicament container 7a, a delivery member 7b, according to the present example a needle, and a delivery member shield 7c. The delivery member shield 7c may be a flexible needle shield (FNS) or a rigid needle shield (RNS). Rigid needle shields typically comprise a flexible inner member and a rigid outer member configured to receive the flexible inner member.

The medicament delivery member device furthermore includes a cap assembly 9, including a cap 11 and a tubular remover 13. The cap assembly 9 is configured to be removably attachable to the main body 3 of the medicament delivery device 1. The cap 11 is configured to receive the remover 13. The cap assembly 9 is configured to be mounted to a proximal end of the housing 3, thereby covering the delivery member cover 5, and the delivery member 7b.

Figure 2:
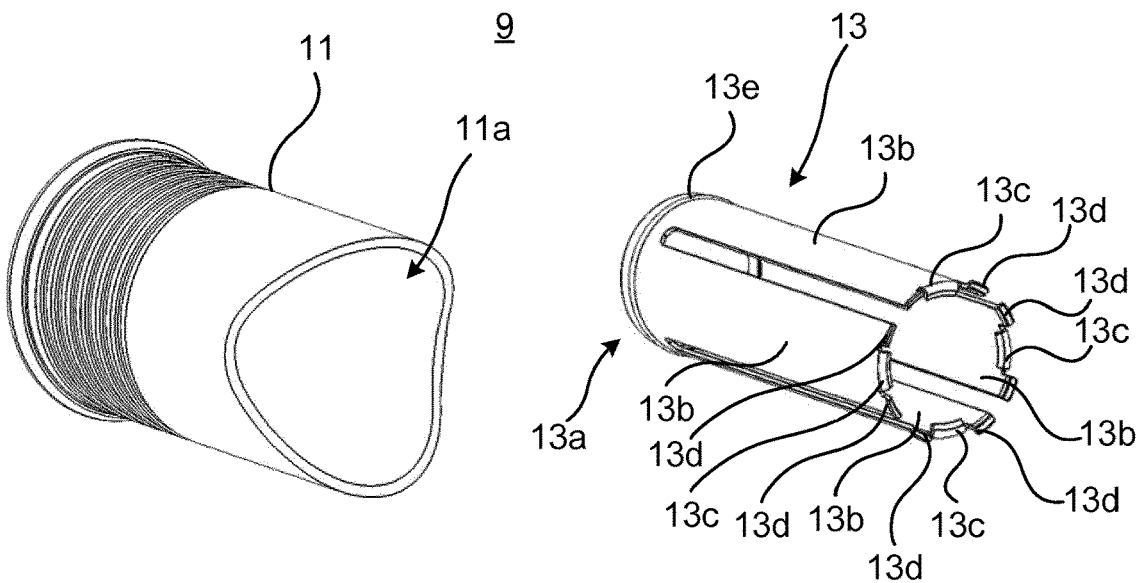
FIG. 2 shows a perspective view of a cap assembly.
Figure 3:
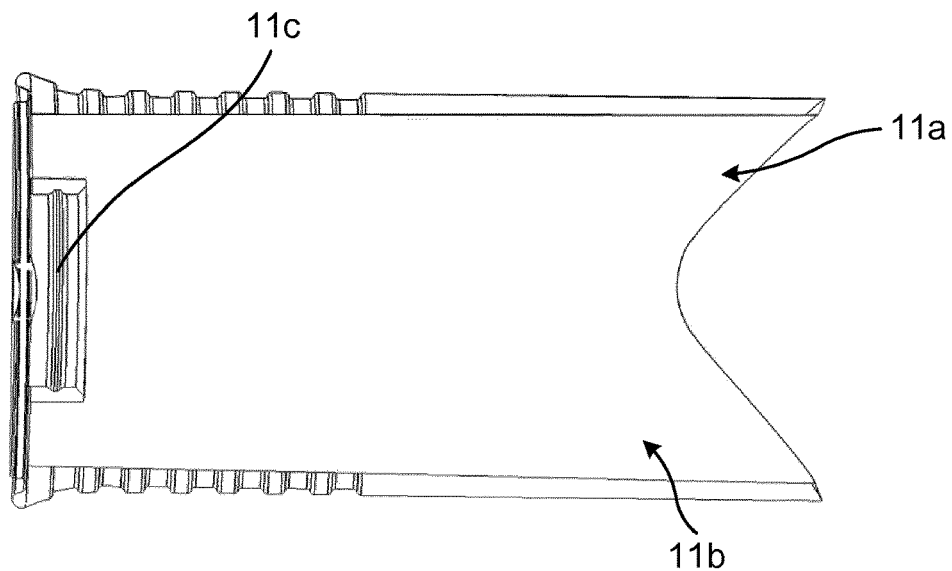
FIG. 3 is a longitudinal section of a cap of the cap assembly in FIG. 2.

FIG. 2 shows a perspective view of a rear side, or distal side, of the cap 11 and of the remover 13. The cap 11 is tubular and has a distal opening 11a, forming a channel 11b, shown in FIG. 3, extending axially from the distal end of the cap 11 to a proximal end thereof. The remover 13 is configured to be received in the channel through the distal opening 11a. The remover 13 is furthermore configured to be fixedly attached inside the cap 11, to prevent axial movement of the remover 13 relative to the cap 11. Hereto, according to one variation the remover 13 may have a proximal end 13a provided with a circumferentially extending rib 13e and the cap 11, in particular the channel 11b, or a structure inside the channel 11b, may have inner walls provided with a circumferential groove 11c, as shown in FIG. 3, configured to receive the rib 13e. Other, alternative means for attaching the remover to the cap include for example glue or a snap-fit configuration.

The remover 13 has a plurality of radially flexible legs 13b, each extending from the proximal portion 13a to a distal end of the remover 13. The remover 13 furthermore has a plurality of grippers 13c and guide fingers 13d. The grippers 13c extend radially inwards in the distal direction. The grippers 13c are configured to engage with the delivery member shield 7c when the medicament delivery device 1 is in an assembled state and the cap assembly 9 is removed from the housing 3. The grippers 13c may for example have a hook-like structure or shape. The grippers 13c may according to one variation be provided at a distal end portion of the legs 13b.

The guide fingers 13d extend radially outwards in the distal direction. The guide fingers 13d extend beyond the grippers 13c in the distal direction. The guide fingers 13d form the distal end of the remover 13.

According to the example shown in FIG. 2, each leg 13b has at least one gripper 13c and a guide finger 13d. For example, each leg 13b may have one gripper 13c and two guide fingers 13d, with one guide finger 13d being provided on either side of the gripper 13c. Each guide finger 13d of the leg 13b is arranged adjacent to the corresponding gripper 13c, in the circumferential direction of the remover 13. Other gripper-guide finger configurations are however also envisaged.

Figure 4:
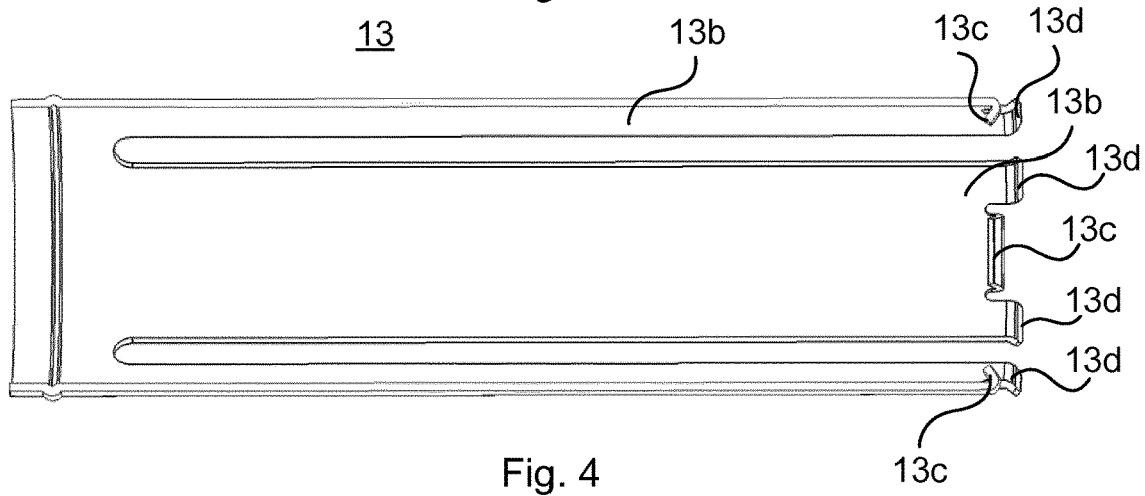
FIG. 4 is a longitudinal section of a remover of the cap assembly in FIG. 2.
Figure 5:
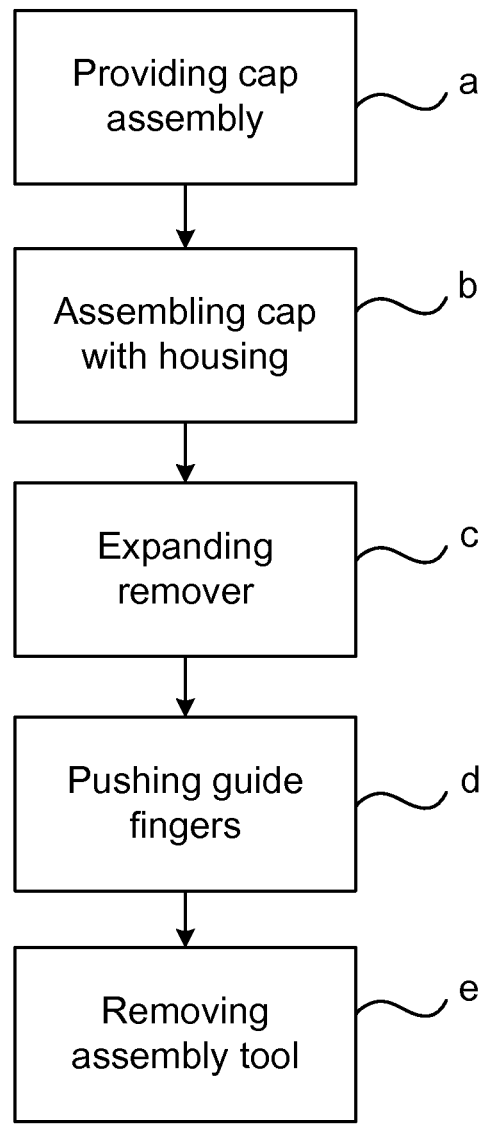
FIG. 5 is a flowchart of a method of assembling a sub-assembly of a medicament delivery device.

FIG. 4 shows a longitudinal section of the remover 13. The grippers 13c are inclined radially inwards in the distal direction and the guide fingers 13d are inclined radially outwards in the distal direction. Each gripper 13c forms an acute angle α with the inner surface of the leg 13b to which the gripper 13c belongs and each guide finger 13d forms an obtuse angle β, both angles α and β shown in FIG. 7b, essentially equal to 180°-α, with the outer surface of the leg 13b to which the guide finger 13d belongs. Hence, according to one variation, the radial inwards inclination of the grippers 13c is the same, or essentially the same, as the radial outwards inclination of the guide fingers 13d. According to the example shown in FIG. 4, the radially outwards inclination of the guide fingers 13d commences in axial level with or distally beyond the most distal point of the grippers 13c. According to another variation, the radial inwards inclination of the grippers differs from the radial outwards inclination of the guide fingers.

With reference to FIGS. 5-8, a method of assembling a sub-assembly 15 comprising the cap assembly 9 and the housing 3 will now be described. FIG. 6a shows a longitudinal section of a proximal portion of a sub-assembly 15 comprising the housing 3 and the cap assembly 9. The exemplified sub-assembly 15 furthermore includes the delivery member cover 5, which is biased in the proximal direction by means of a resilient member, such as a spring. The housing 3 is furthermore provided with an internal structure 3a. According to the present example, the internal structure 3a forms part of the housing 3. It is however envisaged that the internal structure alternatively could form part of a medicament container holder, or of the delivery member cover.

In a step a) the cap assembly 9 and the housing 3 are provided.

In a step b) the cap 11, with the remover 13 attached thereto, is assembled with the housing 3 by pushing the remover 13 into the housing 3. Hereto, the cap assembly 9 is brought over the proximal end of the housing 3. There is a radial distance between the outer surface of the remover 13 and the inner surface of the cap 11, which allows the proximal end of the housing 3 to be received therebetween. Moreover, the delivery member cover 5 is also configured to be received therebetween. At this point, the remover 13 has generally not been moved fully distally.

Figure 6:
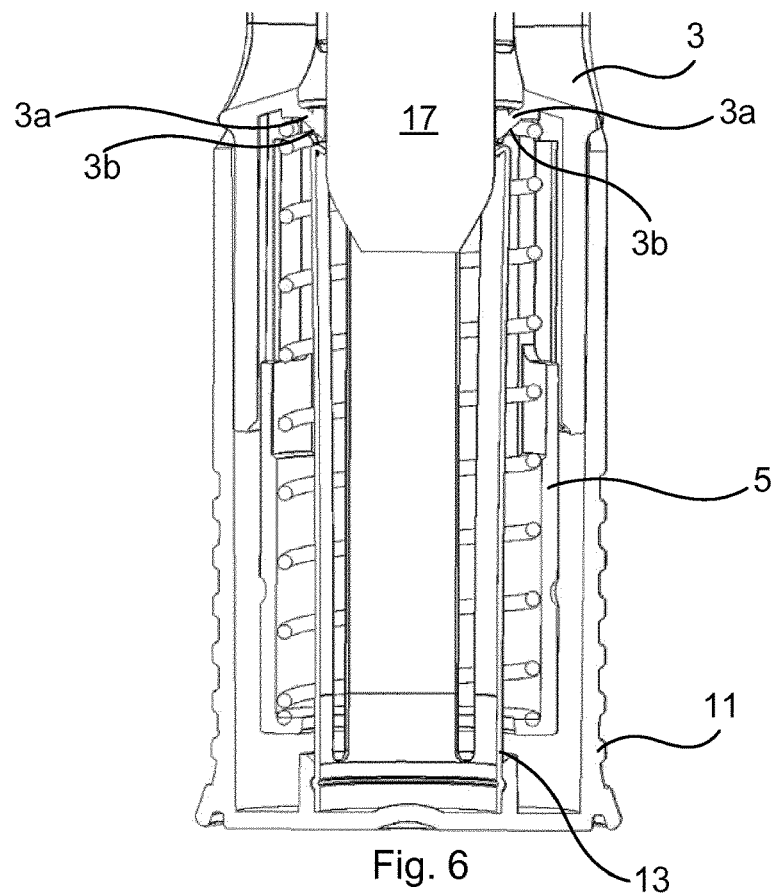
FIG. 6 is a longitudinal section of a portion of a sub-assembly of the medicament delivery device in FIG. 1 when the cap assembly is being assembled with a housing.

As shown in FIG. 6 an assembly tool 17, having a proximal end which increases in diameter in the distal direction is brought into the housing 3, from a distal end thereof.

In a step c) the remover 13 is expanded radially by means of the assembly tool 17. The assembly tool 17 is hence pushed or brought in between the legs 13b of the remover 13 as the assembly tool 17 is moved proximally inside the housing 3. Initially, the assembly tool 17 will have no contact with the legs, due to the smaller diameter at the proximal end of the assembly tool 17. At one point the assembly tool 17 will have moved far enough into the remover 13 so that the diameter of the assembly tool 17 will contact the inner surface of the legs 13b and expand the legs 13b radially. The legs 13b will expand enough to slide over the internal structure 3a when the remover 13 is moved further into the housing 3, in step d) described below.

In a step d) the remover 13 is pushed further into the housing 3 and the guide fingers 13d are thus pushed against a proximal inclined surface of the internal structure 3a whereby the legs 13b of the remover 13 are able to maintain their expanded position. This fixed position of the legs 13b may be obtained because of the frictional attachment of the cap 11 to the housing 3, which maintains the axial position of the cap assembly 9 relative to the housing 3.

Figure 7A:
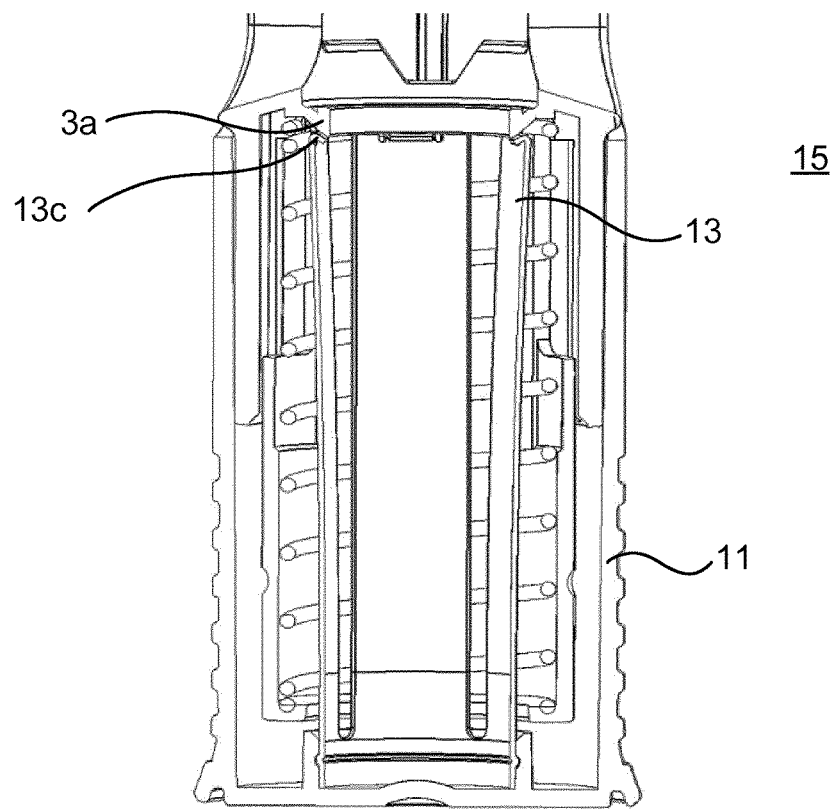
FIG. 7a shows when the cap assembly has been assembled with the housing.
Figure 7B:
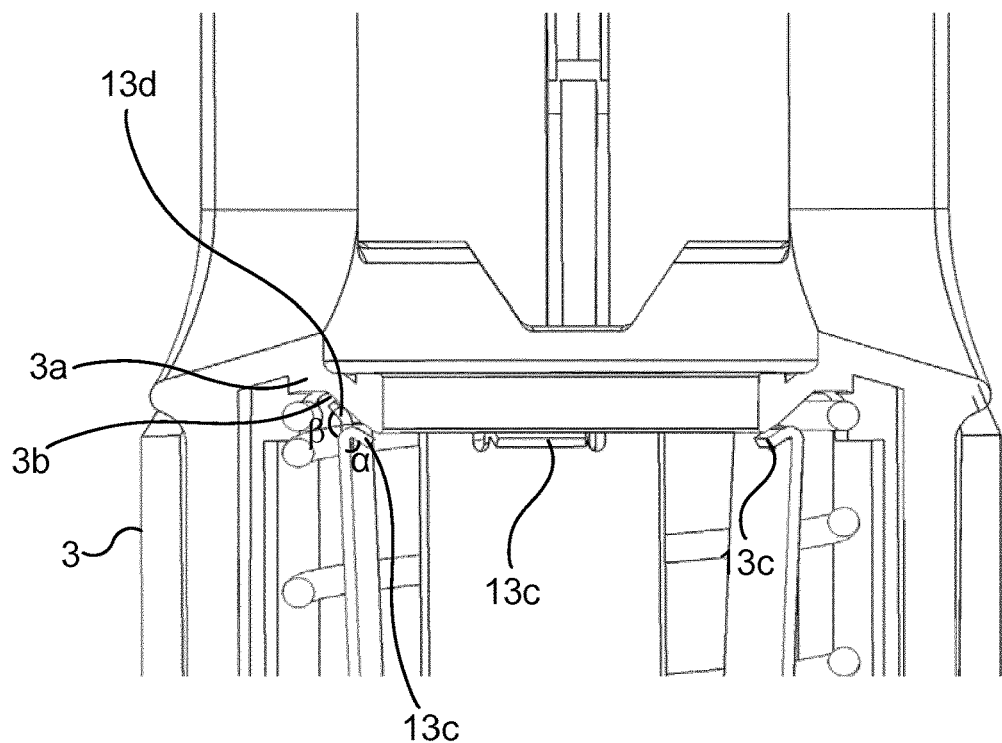

FIG. 7b shows a close-up view of a region of the sub-assembly 15 including the cooperation between the proximal inclined surface 3b of the internal structure 3a and the guide fingers 13d. The internal structure 3a is essentially a flange provided inside the housing 3, according to the example on the inner surface of the housing 3. The internal structure has a proximal inclined surface 3b which is sloping or is inclined, and extends circumferentially The inclination of the proximal inclined surface 3b has an increasing diameter of the internal structure 3a in the distal direction. The assembly tool 17 may have an outer diameter which is slightly smaller than the inner diameter of the internal structure 3a. The inner surfaces of the expanded legs 13b will thus be essentially the same as the inner diameter of the internal structure 3a when the assembly tool 17 has been fully inserted into the remover 13.

Due to the inclined design of the proximal inclined surface 3b, the radially outwards extending guide fingers 13d are able to slide over the proximal inclined surface 3b, thereby allowing the legs 13b to gradually expand as the cap assembly 9 is pushed further in the distal direction.

In a step e) the assembly tool 17 is removed from the housing 3. The assembly tool 17 is removed by moving the assembly tool 17 in the distal direction out from the housing 3, as shown in FIG. 7a.

Figures 8, 9:
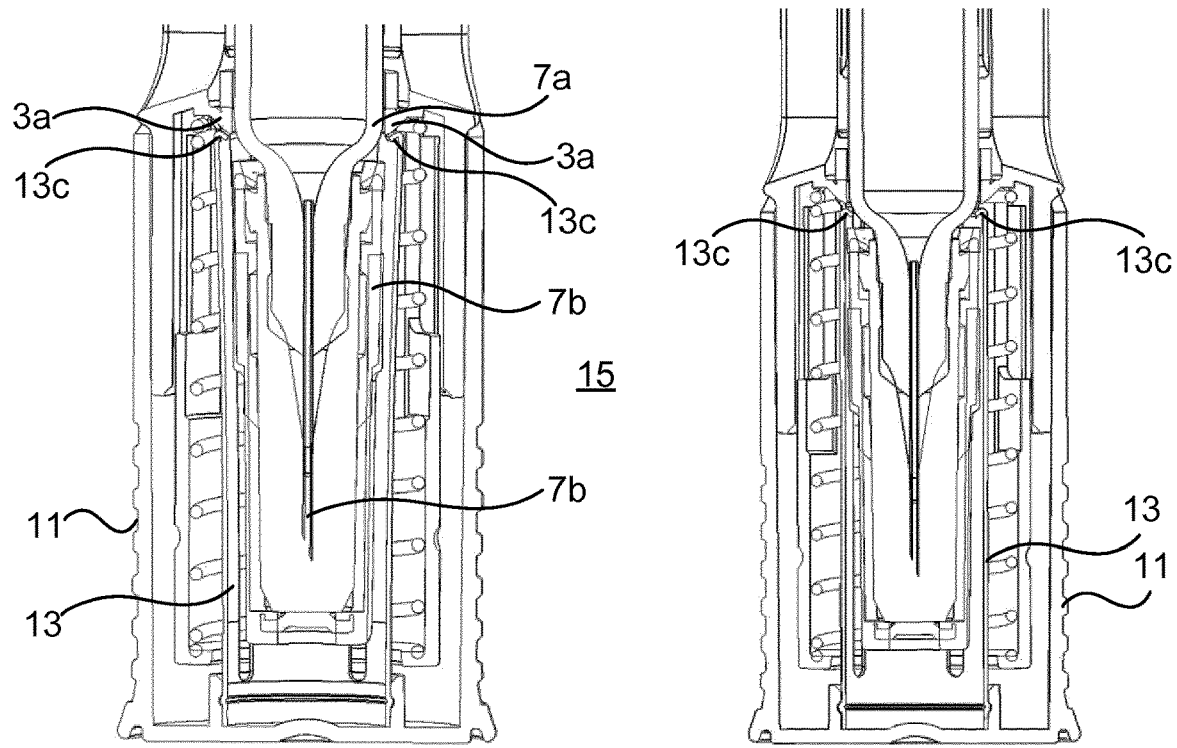
FIG. 8 shows when the remover has received a portion of a medicament container assembly.
FIG. 9 shows when the cap assembly is moved proximally relative to the housing.

When the sub-assembly 15 has been set in the state shown in FIG. 7a, the medicament container assembly 7 may be inserted therein. The medicament container assembly 7 may be inserted through the rear end, or distal end, of the housing 3 and brought forward in the proximal direction through the housing 3 until the delivery member 7b with the delivery member shield 7c protecting it, is received by the remover 13, as shown in FIG. 8. Due to the radially expanded state of the legs 13b, a neck portion of the medicament container 7c as well as the delivery member shield 7b is able to slide past the remover 13 without physical contact. The sub-assembly 15 may subsequently be assembled with the "power pack" to obtain a fully assembled medicament delivery device 1.

According to the example shown in FIG. 8, the remover 13 has a longer axial extension than the delivery member shield 7c, which is fully received by the remover 13. Moreover, the internal structure 3a is arranged distally from the distal edge or rim of the delivery member shield 7c when the medicament container assembly 7 has been installed in the sub-assembly 15. The grippers 13c are arranged distally beyond the distal edge or rim of the delivery member shield 7c, allowing the grippers 13c to engage with the distal edge or rim when the legs 13b are moved radially inwards upon removal of the cap assembly 9, as will be described in more detail in the following. It is to be noted that other variations are also possible; the grippers may according to one example not extend distally beyond the distal edge or rim of the delivery member shield, but may instead engage with an outer peripheral surface of the delivery member shield.

FIG. 9 shows a situation when the cap assembly 9 is being removed from the housing 3, i.e. when the medicament delivery device 1 has been fully assembled and is ready to be used by a user. The cap 11 is thus being pulled in the proximal direction, as shown by the arrow, or equivalently the housing 3 is being pulled in the distal direction relative to the cap assembly 9. Since the remover 13 is fastened to, or immovably attached to the cap 11, the remover 13 is moved concurrently with the cap 11. As the remover 13 moves proximally relative to the internal structure 3a, the guide fingers 13d will move proximally along the inclined proximal inclined surface 3b of the internal structure 3a, causing the legs 13b to flex radially inwards towards their default positions. The grippers 13c will thus also be flexed radially inwards.

Figure 10:
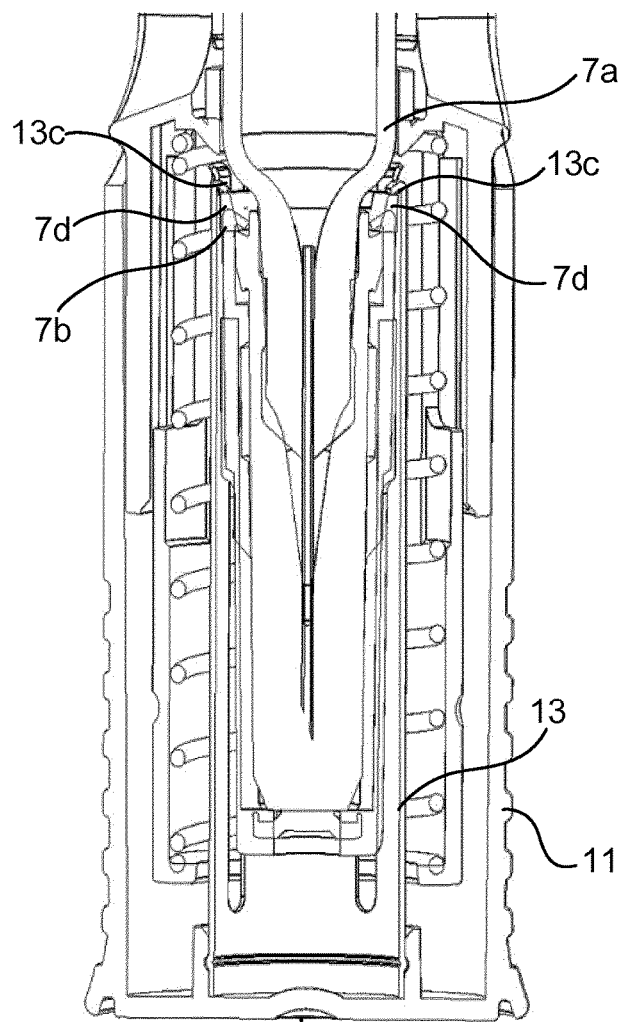
FIG. 10 shows when the remover has engaged with a delivery member shield.

In FIG. 10, the cap assembly 9 has been moved further in the proximal direction and the legs 13b have thus moved further radially inwards. The grippers 13c have in particular moved in behind the distal edge or rim 7d of the delivery member shield 7c.

Figure 11:
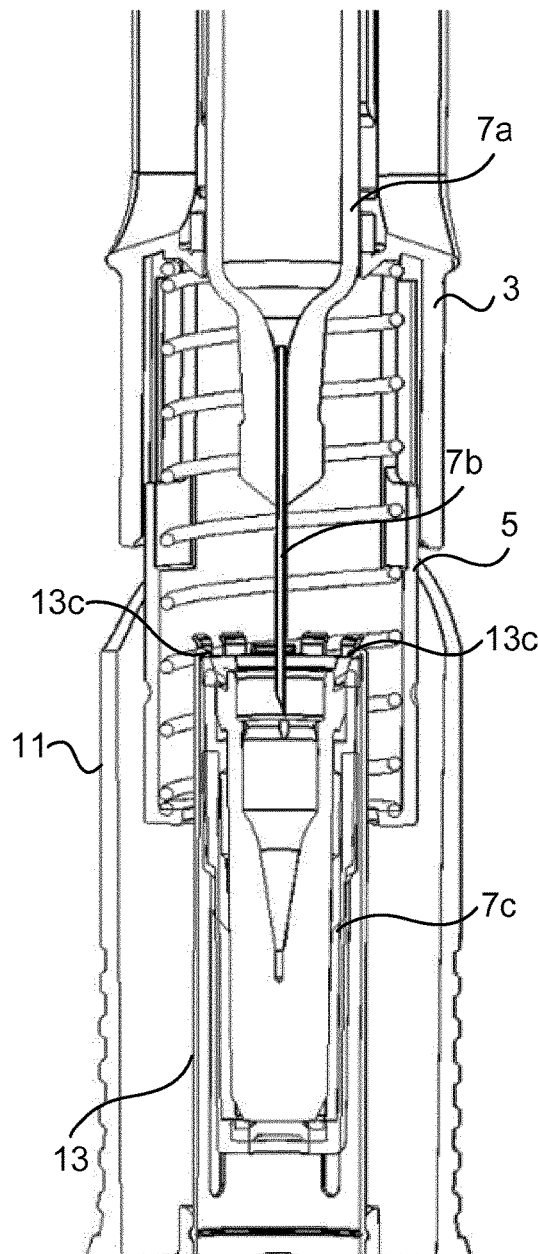
FIG. 11 shows when the remover has removed the delivery member shield from a medicament container.

In FIG. 11, the cap 11 has been removed from the housing 3, and due to the engagement of the grippers 13c with the delivery member shield 7c, the delivery member shield 7c has been removed from the medicament delivery container 7a. When the cap assembly 9 has been fully removed, the delivery member cover 5 may be moved in the distal direction to expose the delivery member 7b, and to initiate medicament administration.

The inventive concept has mainly been described above with reference to a few examples. However, as is readily appreciated by a person skilled in the art, other embodiments than the ones disclosed above are equally possible within the scope of the inventive concept, as defined by the appended claims.

The invention claimed is:

1. A sub-assembly for a medicament delivery device, comprising:
   a cap having a tubular body provided with a distal opening, the cap being configured to be mounted to a proximal end of the medicament delivery device, and
   a tubular remover configured to be received in the distal opening of the cap, the remover having a proximal end portion configured to be fixedly attached to the cap,
   wherein the remover has a plurality of radially flexible legs extending axially from a proximal end of the remover to a distal end thereof, each leg having a gripper configured to engage with a delivery member shield of the medicament delivery device, and each leg having a guide finger configured to extend distally beyond the grippers for cooperating with an internal structure located on an inside of a housing of the medicament delivery device to guide radial expansion of the legs when the remover is mounted in the medicament delivery device, and
   wherein each guide finger is located adjacent to, in a circumferential direction, a gripper.

2. The sub-assembly as claimed in claim 1, wherein each gripper extends radially inwards to allow engagement with the delivery member shield.

3. The sub-assembly as claimed in claim 2, wherein each gripper has a hook-like structure.

4. The sub-assembly as claimed in claim 1, wherein each guide finger extends radially outwards.

5. The sub-assembly as claimed in claim 4, wherein each guide finger gradually increases the diameter of the remover in a distal direction.

6. The sub-assembly as claimed in claim 1, wherein for each leg the gripper forma an acute angle relative to an inner surface of the leg and the guide finger forms an obtuse angle relative to the inner surface of the leg.

7. The sub-assembly as claimed in claim 1, wherein the plurality of legs are equally spaced around circumference defined by the grippers.

8. The sub-assembly as claimed in claim 1, wherein each leg has a distal end portion, wherein each gripper is provided on the distal end portion of the respective leg, enabling engagement with a distal edge of the delivery member shield.

9. The sub-assembly as claimed in claim 1, wherein the internal structure has a proximal inclined surface with a first inclination relative to a central axis of the housing, and wherein the guide fingers have the same inclination as the proximal inclined surface has.

10. The sub-assembly as claimed in claim 1, wherein the proximal inclined surface provides an increased diameter of the internal structure in the distal direction.

11. A medicament delivery device comprising a sub-assembly as claimed in claim 1.

12. The medicament delivery device as claimed in claim 11, wherein the medicament delivery device is one of an injector and an inhaler.

13. The medicament delivery device as claimed in claim 12, wherein the medicament delivery device comprises a medicament container assembly, which includes a medicament container, a delivery member and the delivery member shield.

14. The medicament delivery device as claimed in claim 11, wherein the medicament delivery device comprises at least one of a flexible needle shield, a sheath, or a rigid needle shield.

15. The medicament delivery device as claimed in claim 11, wherein the medicament delivery device comprises a medicament container assembly, which includes a medicament container, a delivery member and the delivery member shield.

16. The medicament delivery device as claimed in claim 15, wherein the medicament delivery device comprises at least one of a flexible needle shield, a sheath, or a rigid needle shield.

17. The medicament delivery device as claimed in claim 11, wherein the medicament delivery device comprises at least one of a flexible needle shield, a sheath, or a rigid needle shield.

18. A method of assembling a sub-assembly of a medicament delivery device, comprising:
   a) providing a cap assembly comprising:
   a cap having a tubular body provided with a distal opening, the cap being configured to be mounted to a proximal end of the medicament delivery device, and
   a tubular remover received in the distal opening of the cap, the remover having a proximal end portion fixedly attached to the cap,
   wherein the remover has a plurality of radially flexible legs extending axially from a proximal end of the remover to a distal end thereof, each leg having a gripper configured to engage with a delivery member shield of the medicament delivery device, and each leg having a guide finger configured to extend distally beyond the grippers for cooperating with an internal structure of the medicament delivery device to guide radial expansion of the legs when the remover is mounted in the medicament delivery device,
   b) assembling the cap with a housing having the internal structure arranged inside the housing and provided with a proximal inclined surface, by pushing the remover into the housing,
   by pushing the remover into the housing,
   c) expanding the remover radially by means of an assembly tool inserted into the housing from a distal end thereof,
   d) pushing the guide fingers against the proximal inclined surface of the internal structure whereby the legs of the remover maintain their expanded position, and e) removing the assembly tool from the housing.

19. A medicament delivery device, comprising:

a cap having a tubular body provided with a distal opening, the cap being configured to be mounted to a proximal end of the medicament delivery device;

a tubular remover configured to be received in the distal opening of the cap, the remover having a proximal end portion configured to be fixedly attached to the cap; and a housing having an internal structure arranged inside the housing and provided with a proximal inclined surface;

wherein the remover has a plurality of radially flexible legs extending axially from a proximal end of the remover to a distal end thereof, each leg having a gripper configured to engage with a delivery member shield of the medicament delivery device, and each leg having a guide finger configured to extend distally beyond the grippers for cooperating with the internal structure of the medicament delivery device to guide radial expansion of the legs when the remover is mounted in the medicament delivery device, and wherein the guide fingers are configured to cooperate with the proximal inclined surface of the internal structure, to maintain a radial expansion of the legs of the remover.

\* \* \* \* \*